(12) United States Patent
Tambe

(10) Patent No.: US 10,105,054 B2
(45) Date of Patent: Oct. 23, 2018

(54) SYSTEM, SOFTWARE AND METHOD OF STREAMING ECG/EKG DATA OVER BLUETOOTH LOW-ENERGY INTERFACE

(71) Applicant: NimbleHeart Inc.

(72) Inventor: Sonal Tambe, Saratoga, CA (US)

(73) Assignee: Nimbleheart Inc., Saratoga, CA (US)

( * ) Notice: Subject to any disclaimer, the term of this patent is extended or adjusted under 35 U.S.C. 154(b) by 0 days.

(21) Appl. No.: 14/174,772

(22) Filed: Feb. 6, 2014

(65) Prior Publication Data

US 2014/0221862 A1    Aug. 7, 2014

Related U.S. Application Data

(60) Provisional application No. 61/761,549, filed on Feb. 6, 2013.

(51) Int. Cl.
*A61B 5/00* (2006.01)
*A61B 5/0432* (2006.01)

(52) U.S. Cl.
CPC .......... *A61B 5/0006* (2013.01); *A61B 5/0432* (2013.01)

(58) Field of Classification Search
CPC .............................. A61B 5/0452; A61B 5/044
USPC .................................................. 600/483, 523
See application file for complete search history.

(56) References Cited

U.S. PATENT DOCUMENTS

2012/0059271 A1* 3/2012 Amitai ................. A61B 5/0404
600/509
2014/0039337 A1* 2/2014 Kampman ........... A61B 5/0022
600/523

* cited by examiner

*Primary Examiner* — Nadia A Mahmood
(74) *Attorney, Agent, or Firm* — Timothy Dennison

(57) ABSTRACT

A system, software and method of streaming ECG/EKG data over Bluetooth low-energy interface.

11 Claims, 4 Drawing Sheets

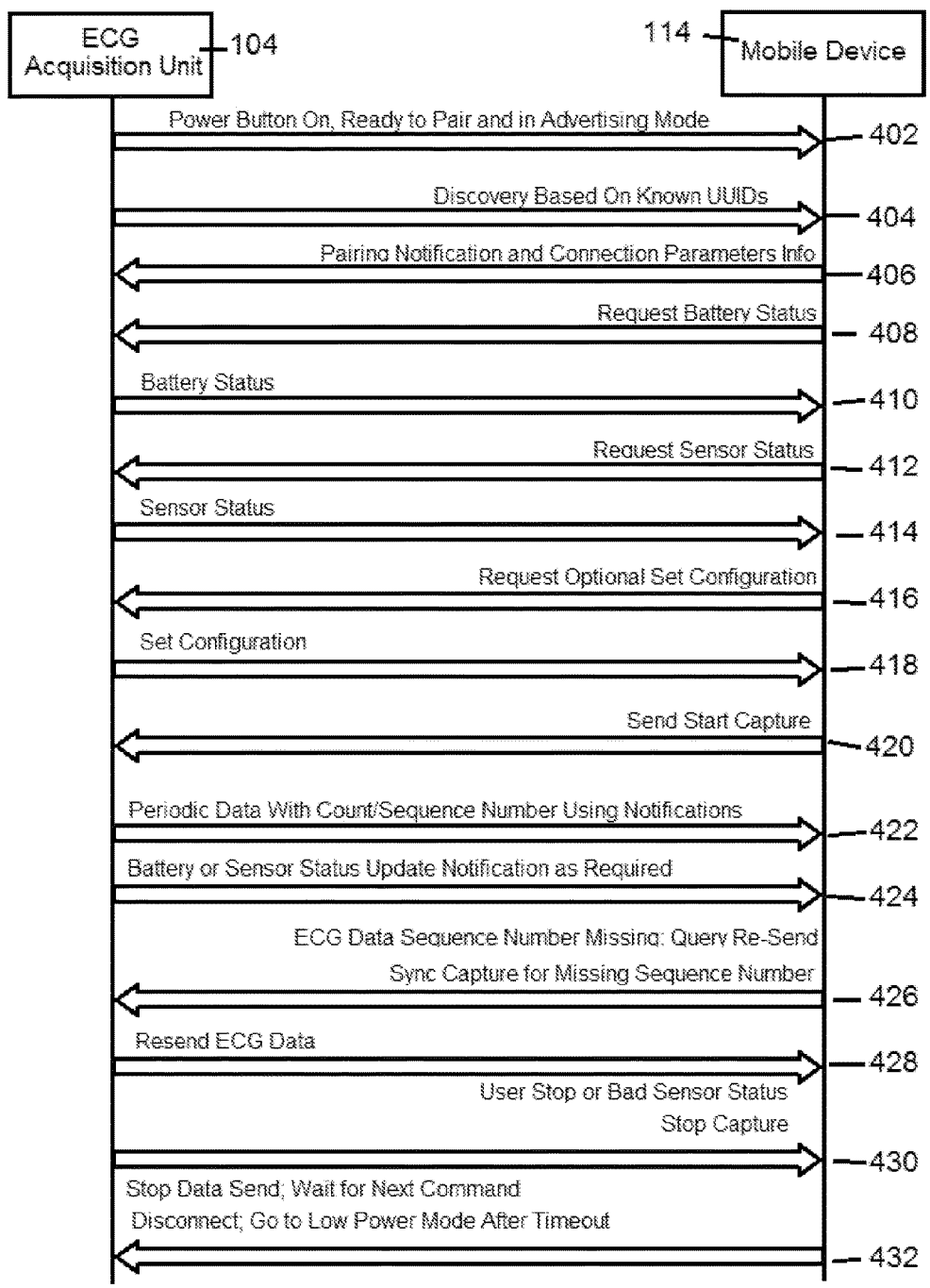

SYSTEM, SOFTWARE AND METHOD OF STREAMING ECG/EKG DATA OVER BLUETOOTH LOW-ENERGY INTERFACE

BACKGROUND

Episodic cardiac symptoms, such as arrhythmia, are triggered by a wide variety of events including stress. In order for physicians to effectively diagnose the cause of the attack, they must analyze the particular pattern of the heartbeat irregularity. Electrocardiographic data is commonly used in such an analysis. Unfortunately, most arrhythmias are spontaneous and unpredictable, making detection nearly impossible while at the physician's office.

Portable electrocardiogram monitoring and recording devices for use by persons in outpatient environments have long been known. These devices include those which can be conveniently clipped on to a user's belt for wear throughout his daily routine. With the unit constantly in place, the user can simply press a button to start data recording whether it be periodic charting data or to signal the onset of an arrhythmia attack.

Typically, this type of portable unit is equipped with a sufficient amount of internal memory to record several minutes of ECG data. The unit can then be taken into the physician's office where inspection can be made of the electrocardiogram pattern recorded during the arrhythmia episode. Recent ECG recording devices have been equipped with wireless interfaces to relieve the user of the burden of traveling to the physician's office or physically connecting to a computer or phone line. Instead, the wireless interface permits the ECG data to be transmitted to the physician's office or to an analysis unit over a standard wireless network.

Clinical quality ECG/EKG data can have a bandwidth of 4 to 64 Kilo Bits per Sec depending upon the sampling rate. For continuous monitoring applications this implies tremendous memory and processing power requirements. Modern mobile platforms like smart phones and tablets are equipped with good processing power and gigabytes of memory that can be used to analyze and store ECG data.

However, in order to use this capability of a mobile device, an ECG acquisition device needs to send real time ECG data reliably to the mobile device. Older acquisition units may stream ECG data real time using wired interface like USB or Bluetooth Classic technology.

Bluetooth Low-Energy (BLE), which is a part of the Bluetooth 4.0 specification, is a more efficient wireless interface that can achieve the same data streaming performance with optimized battery life and ease of usage.

However, the currently published profiles over BLE don't support real-time streaming of ECG data. Some new ECG signal acquisition devices process the ECG signal locally to extract heart rate information and then send it over BLE interface using a heart rate profile.

By streaming raw real-time ECG data over BLE interface this invention allows a more compact implementation of ECG acquisition unit with longer battery life while providing the visibility into and flexibility of analysis of full raw ECG data on a mobile platform for continuous monitoring.

In this respect, before explaining at least one embodiment of the invention in detail, it is to be understood that the invention is not limited in its application to the details of construction and to the arrangement of the components set forth in the following description or illustrated in the drawings. The invention is capable of other embodiments and of being practiced and carried out in various ways. In addition, it is to be understood that the phraseology and terminology employed herein are for the purpose of description and should not be regarded as limiting.

SUMMARY OF THE INVENTION

In one embodiment, a system for streaming real-time ECG data captured by ECG sensors efficiently and reliably to mobile platforms over BLE interface is defined.

In one embodiment, a software protocol that can be used for streaming real-time ECG data captured by ECG sensors efficiently and reliably to mobile platforms over BLE interface is defined.

In one embodiment, a method of streaming real-time ECG data captured by ECG sensors efficiently and reliably to mobile platforms over BLE interface is defined.

In one or more embodiments, the software protocol is optimized for the BLE interface to facilitate reliable real-time transmission of raw ECG data to a mobile platform.

In one or more embodiments, the BLE software may run on one or more of the following mobile operating systems including, but not limited to, iOS, Android, Windows Phone and BlackBerry.

In one or more embodiments, the BLE software may run on one or more of the following operating systems including, but not limited to, Linux, OS X and Windows.

In one or more embodiments an ECG or EKG signal is acquired by an acquisition unit. This signal may be transmitted to a mobile device for recording, analysis, storage or retransmission.

In one or more embodiments, acquisition unit may act as a server that generates and streams ECG data and then communicates this data to the mobile device or other devices as such.

In a server mode, a BLE ECG profile may be acquired stored, manipulated or accessed through the Bluetooth stack and manipulated or analyzed by the real-time operating system (RTOS) software and/or platform.

The acquisition unit server may include, in one embodiment, the ECG profile components present in the device firmware such as: ECG transmission data buffering and sequence counter handling, device status transmission management, reception command handling, encryption and decryption, all written within the Bluetooth 4.0 embedded stack.

In one or more embodiments, the mobile device may act as a client and communicate with the acquisition unit or other devices as such.

In client mode, the BLE ECG profile may be manipulated or accessed through the Bluetooth 4.0 application programming interface (API) on the mobile operating system.

In client mode, in one embodiment, the ECG profile components of the iOS application may include a module for ECG data reception handling and sequence counter management, reception status handling, transmission command management, encryption and decryption, all on the iOS core Bluetooth framework.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention.

Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Other objectives, features and advantages of the invention will become apparent from the following description and drawings wherein.

BRIEF DESCRIPTION OF THE DRAWINGS

FIG. 4 is a graphical representation of the data and command flow if the ECG data streaming of an embodiment.

DETAILED DESCRIPTION

Figure 1:
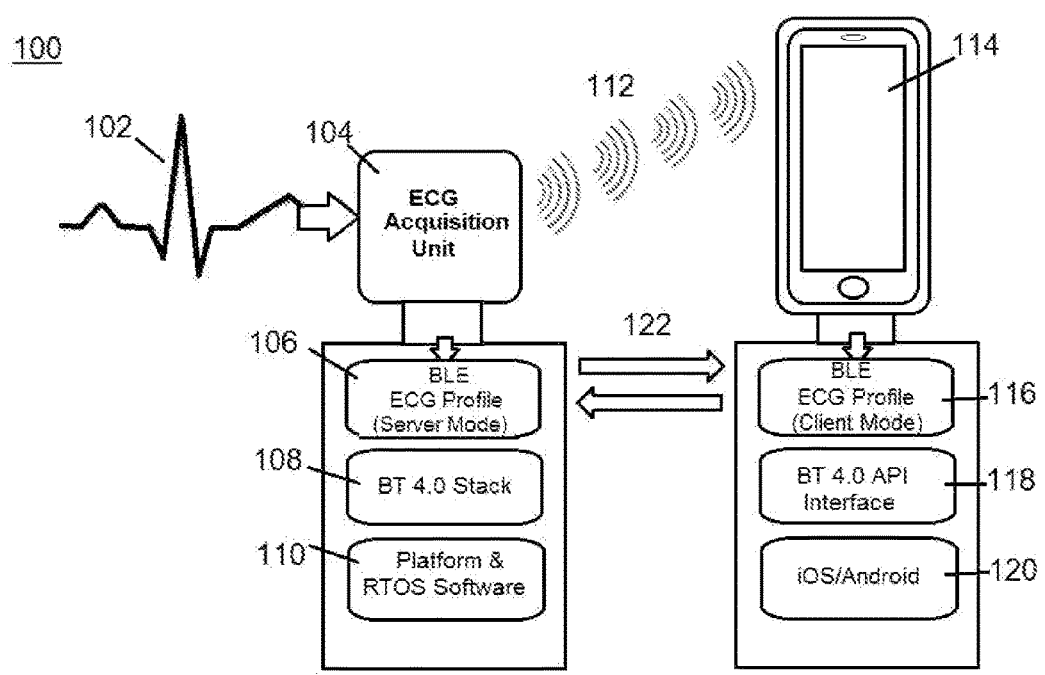
FIG. 1 is a graphical representation of the ECG streaming components of an embodiment.

Referring now to FIG. 1, in one embodiment, the real-time BLE ECG data streaming system consists of an ECG acquisition unit 104 wherein a data signal 102 is acquired.

The acquired signal 102 may be stored and compared to a BLE ECG profile 106 programmed into the BT 4.0 stack 108 on top of the platform and RTOS software 110.

This information may be transmitted wirelessly 112 to a mobile device 114. The transmission 112 may be streamed or sent in discrete packets.

The acquisition unit 104 may also exchange command and status data 122 with the mobile device 114.

The mobile device 114 may act as a client and may store a, or have a stored, BLE ECG profile 116 accessible through a Bluetooth 4.0 API 118 written on the mobile device operating system 120.

Figure 2:
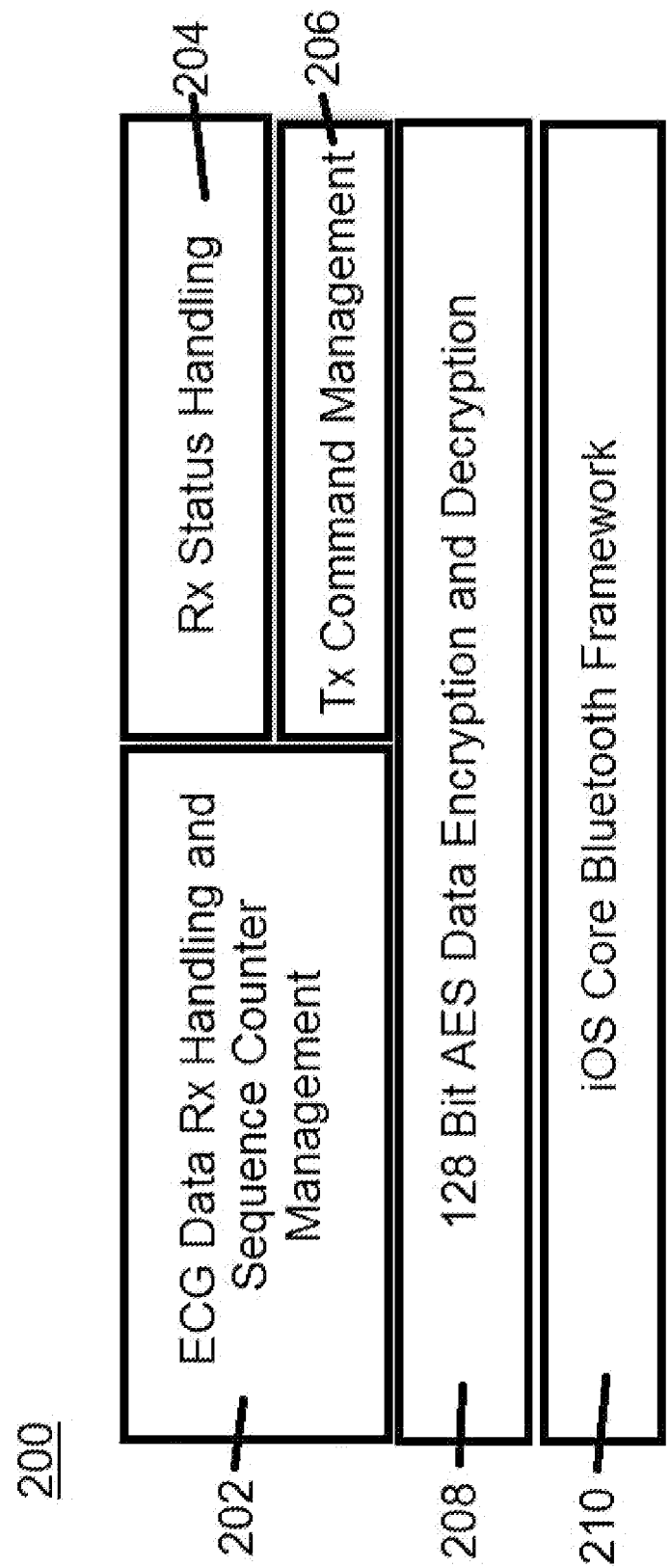
FIG. 2 is a graphical representation of the ECG Profile Components of the iOS client application embodiment.

Referring now to FIG. 2, in one embodiment, the mobile device application may act as a client. The ECG components 200 may comprise an ECG data reception handling and sequence counter management module 202, a reception status handling module 204, a transmission command module 206, an encryption and decryption module 208 and a mobile device Bluetooth framework 210.

Figure 3:
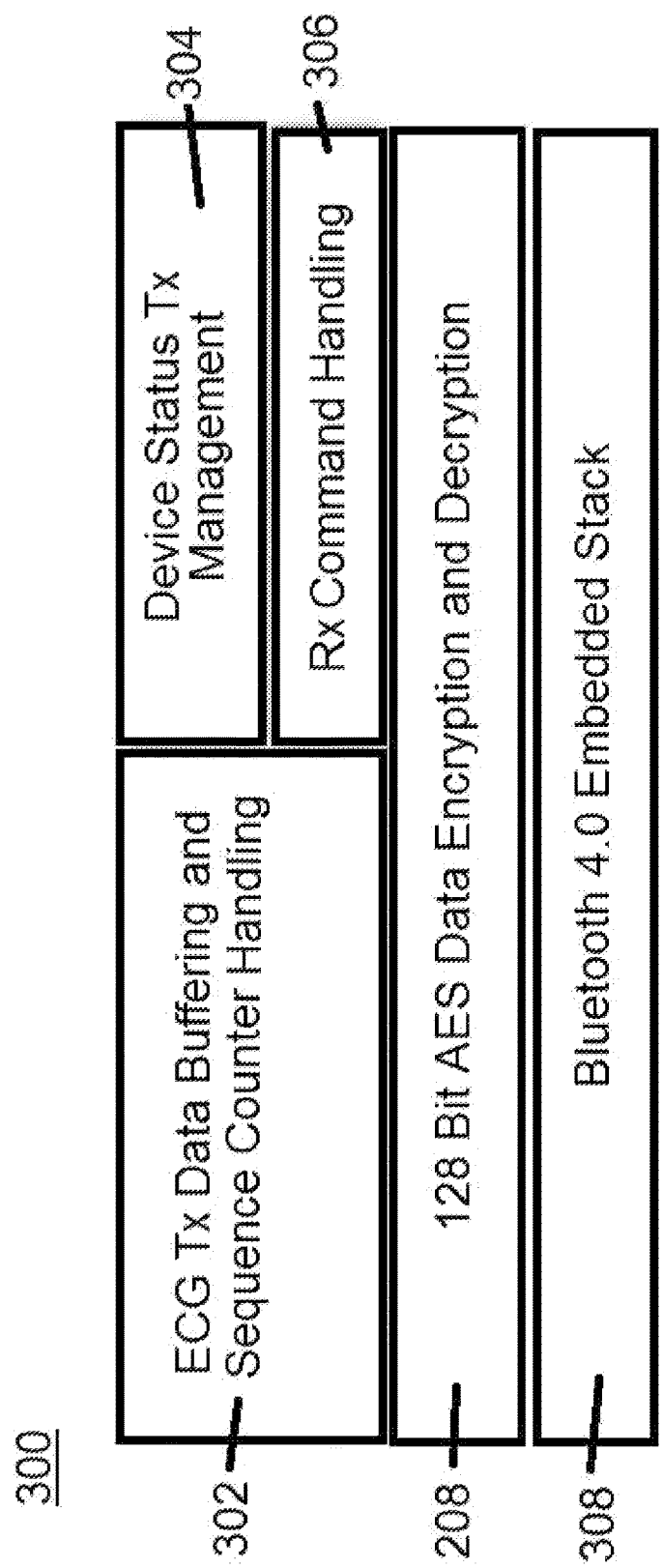
FIG. 3 is a graphical representation of the ECG Profile Components in a device firmware server embodiment.

Referring now to FIG. 3, in one embodiment, the device firmware may act as a server.

The ECG components 300 may comprise an ECG data transmission buffering and sequence counter handling module 302, a device status transmission management module 304, a reception command handling module 306, an encryption and decryption module 208 and a Bluetooth 4.0 embedded stack 308.

Referring now to FIG. 4, in one embodiment, the data and command flow 400 for the ECG data streaming between the ECG acquisition unit 104 and the mobile device 114 may include a power on, ready-to-pair, advertising mode 402. Known devices signified by their universally unique identification (UUID) may be discovered 404. Pairing notification and connection parameters 406 may then be exchanged. A battery status request 408 and sensor status request 412 may be transmitted and the respective battery status 410 and sensor status 414 returned.

An optional configuration setting request 416 and configuration settings 418 transmission may also be available.

A start capture command 420 commences the acquisition of data with periodic data updates 422, and battery and sensor status updates 424, received as necessary or scheduled.

An error tag for missing sequential data 426 and a resending of the data 428 allows for error correction and incomplete transmissions.

A stop capture command 430 and a disconnect or time out feature 432 may also be available.

I claim:

1. A system for streaming real-time ECG data to mobile platforms over a Bluetooth Low-Energy (BLE) interface comprising:
    at least one ECG data acquisition unit,
    at least one BLE-enabled mobile computational device,
    a means for the storage of the ECG data,
    a means for processing the ECG data; and
    a software protocol wherein the at least one ECG data acquisition unit may communicate with the at least one BLE-enabled mobile computational device and the ECG data may be transmitted to, processed by, analyzed by, stored on or re-transmitted from the BLE-enabled mobile device.

2. The system of claim 1, wherein the means for the storage of the ECG data is inherent in the at least one ECG acquisition unit.

3. The system of claim 1, wherein the means for the storage of the ECG data is inherent in the at least one BLE-enabled mobile computational device.

4. The system of claim 1, wherein the means for processing the ECG data is inherent in the at least one ECG acquisition unit.

5. The system of claim 1, wherein the means for processing the ECG data is inherent in the at least one BLE-enabled mobile computational device.

6. A software product, comprising a non-transitory computational device-readable medium in which program instructions are stored, which instructions, when read by the at least BLE-enabled mobile computational device, cause the BLE-enabled mobile computational device to receive ECG data, process the ECG data and produce a report on the acquired data.

7. A method of streaming real-time ECG data to mobile platforms over a Bluetooth Low-Energy (BLE) interface comprising:
    providing at least one ECG data acquisition unit,
    providing at least one BLE-enabled mobile computational device,
    providing a means for the storage of the ECG data,
    providing a means for processing the ECG data; and
    providing a software protocol wherein the at least one ECG data acquisition unit may communicate with the at least one BLE-enabled mobile computational device and the ECG data may be transmitted to, processed by, analyzed by, stored on or re-transmitted from the BLE-enabled mobile device.

8. The method of claim 7 wherein the step of providing the means for the storage of the ECG data further comprises the step of providing a means for storage of the ECG data which is inherent in the at least one ECG acquisition unit.

9. The method of claim 7 wherein the step of providing the means for the storage of the ECG data further comprises the step of providing a means for storage of the ECG data which is inherent in the at least one mobile computational device.

10. The method of claim 7 wherein the step of providing the means for processing the ECG data further comprises the step of providing a means for processing the ECG data which is inherent in the at least one ECG acquisition unit.

11. The method of claim 7 wherein the step of providing the means for processing the ECG data further comprises the step of providing a means for processing the ECG data which is inherent in the at least one mobile computational device.

\* \* \* \* \*